United States Patent [19]

Fleischmann

[11] Patent Number: 5,145,859
[45] Date of Patent: Sep. 8, 1992

[54] METHODS OF TREATING INTERSTITIAL CYSTITIS AND URETHRAL SYNDROME

[75] Inventor: Jonathan D. Fleischmann, Cleveland Heights, Ohio

[73] Assignee: Case Western Reserve University, Cleveland, Ohio

[21] Appl. No.: 672,393

[22] Filed: Mar. 20, 1991

[51] Int. Cl.$^5$ ............................................. A61K 31/44
[52] U.S. Cl. ................................................. 514/356
[58] Field of Search ........................................ 514/356

[56] References Cited

U.S. PATENT DOCUMENTS

| | | | |
|---|---|---|---|
| 4,268,518 | 5/1981 | Turner | 424/283 |
| 4,412,986 | 11/1983 | Kawata et al. | 424/80 |
| 4,690,935 | 9/1987 | Taylor et al. | 514/356 |
| 4,696,934 | 9/1987 | Marcoux | 514/277 |
| 4,728,660 | 3/1988 | Haynes et al. | 514/356 |
| 4,749,714 | 6/1988 | Gross et al. | 514/356 |
| 4,765,990 | 8/1988 | Sugimoto et al. | 424/494 |
| 4,776,081 | 9/1988 | Doi et al. | 514/356 |
| 4,778,798 | 10/1988 | Brasey | 514/277 |
| 4,800,081 | 1/1989 | Albreich et al. | 424/129 |
| 4,814,175 | 3/1989 | Tack et al. | 424/453 |
| 4,855,300 | 8/1989 | Nandi et al. | 514/264 |
| 4,869,899 | 9/1989 | Burghart et al. | 424/78 |
| 4,871,545 | 10/1989 | Dethlefsen | 424/470 |
| 4,874,774 | 10/1989 | Ushimaru et al. | 514/356 |
| 4,877,791 | 10/1989 | Sherman | 514/282 |
| 4,880,623 | 11/1989 | Piergiorgio et al. | 424/78 |
| 4,892,730 | 10/1990 | Hegasy | 424/80 |
| 4,894,235 | 1/1990 | Köhne et al. | 424/452 |
| 4,904,699 | 2/1990 | Bauer | 514/972 |

OTHER PUBLICATIONS

Gillenwater, et al., Summary of the National Institute of Arthritis, Diabetes, Digestive and Kidney Diseases Workshops on Interstitial Cystitis, National Institutes of Health, Bethesda, Md, Aug. 28–29, 1987, The Journal of Urology, vol. 140, pp. 203–206, Jul. 1988.

Harvey L. Gordon, et al., Immunologic Aspects of Interstitial Cystitis, The Journal of Urology, vol. 109, pp. 228–233, Feb. 1972.

Philip Hanno, et al., Diagnosis of Interstitial Cystitis, The Journal of Urology, vol. 143, pp. 278–281, Feb. 1989.

J. D. Fleischmann, et al., Measurement and Partial Characterization of an Interleukin-2 Inhibitor (IL--2-IN) In Human Urine, Journal of Biological Regulators and Homeostatic Agents, vol. 4, No. 2, pp. 73–80, Apr. 1990.

W. Bruce Shingleton, et al., Urinary Interleukin-2 Inhibitor and the Voiding Symptoms in Female Patients with Interstitial Cystitis, Seminars in Urology, vol. IX, No. 2, pp. 001–005, May 1991.

M. A. Zar, et al., Effect of Nifedipine on the Contractile Responses of the Isolater Rat Bladder, The Journal of Urology, vol. 143, pp. 835–839, Apr.

Deborah L. Birx, et al., The Interference of T Cell Activation by Calcium Channel Blocking Agents, the Journal of Immunology, vol. 133, No. 6, pp. 2904–2909, Dec. 1984.

Quintina Corteza, et al., Effects of Calcium Channel Blockers in Vivo Cellular Immunity in Mice, Transplantation, vol. 47, No. 2, pp. 339–342, Feb. 1989.

Steven Gillis, et al., T Cell Growth Factor: Paramets of Production and a Quantitative Microassay for Activity, The Journal of Immunology, vol. 120, No. 6, pp. 2027–2032, Jun. 1978.

Kazuo Kasugami, et al., Intestinal Immune Reactivity to Interleukin 2 Differs among Chrohn's Disease, Ulcerative Colitis, and Controls, Gastroenterology, vol. 97, No. 1, pp. 1–9, Jul. 1989.

Joel E. Richter, et al., Oral Nifedipine in the Treatment of Noncardiac Chest Pain in Patients with the Nutcracker Esophagus, Gastroenterology, vol. 93, No. 1, pp. 21–28, Jul. 1987.

Peter H. Stone, M.D., et al., Calcium Channel Blocking Agents in the Treatment of Cardiovascular Disorders. Part II: Hemodynamic Effects and Clinical Applications, Annals of Internal Medicine, vol. 93, No. 6, pp. 886–904, Dec. 1980.

Sami Viskin, M.D., et al., Nifedipine and Ureteral Colic, Annals of Internal Medicine, vol. 105, No. 1, p. 142, Jul. 1986.

A. Tapp, et al., Terodiline: a Dose Titrated, Multicenter Study of the Treatment of Idiopathic Detrusor Instability in Women, the Journal of Urology, vol. 142, pp. 1027–1031, Oct. 1989.

Ramon Perez-Marrero, M.D., et al., Urodynamic Studies in Interstitial Cystitis, Supplement to Urology, vol. XXIX, No. 4, pp. 27–30, Apr. 1987.

Philip M. Hanno, M.D., et al., Medical Treatment of Interstitial Cystitis (Other than Rimso-50/Elmiron), Supplement to Urology, vol XXIX, No. 4, pp. 22–27, Apr. 1987.

(List continued on next page.)

*Primary Examiner*—Frederick E. Waddell
*Assistant Examiner*—Diane Gardner
*Attorney, Agent, or Firm*—Fay, Sharpe, Beall, Fagan, Minnich & McKee

[57] ABSTRACT

According to the invention there is provided various methods of treating mammalian interstitial cystitis and/or urethral syndrome through the use of Nifedipine, a calcium channel antagonist which has been primarily used for the treatment of coronary artery spasms and hypertension. Specifically, the invention is directed to the adminstration of an therapeutically effective amount of Nifedipine to mammals suffering from interstitial cystitis and/or urethral syndrome. The Nifedipine may be administered in admixture with a pharmaceutically acceptable carrier in a unit dosage form. The route of administration is that deemed preferred by the attending physician, with oral administration being preferred.

2 Claims, No Drawings

OTHER PUBLICATIONS

Peters, D. et al., Scand J Urol Nephrol Suppl 87(Suppl):21–33 1984.

Susset, J. et al, J Urol 141(2):408–13 1989.

Ogawa, A. et al, Hinyikika Kiyo 34(4): 739–53 1988.

Nakano, M. et al, Hinyokika Kiyo 34(1): 196–200 1988.

Kontani, H. et al, Japan J Pharmacol 53: 427–433 1990.

Kerstin M. Kindahl-Kiessling, Calcium Dependency of the Binding and Mitogenicity of Phytohemagglutinin, Experimental Cell Research 103, pp. 151–157, 1976.

Gustav, J. V. Nossal, M.D., Ph.D., The Basic Components of the Immune System, The New England Journal of Medicine, pp. 1320–1325, May 21, 1987.

Jonathan D. Fleischmann, M.D., et al., Urinary Interleukins in Patients Receiving Intravesical Bacillus Calmette-Guerin Therapy for Superficial Bladder Cancer, Cancer, vol. 64, No. 7, pp. 1447–1454, Oct. 1, 1989.

J. D. Fleischmann, M.D., et al., Urinary Interleukin-2 Inhibition in Patients with Cystitis, Immunological Investigations, vol. 18, No. 6, pp. 824–831, 1989.

N. T. M. Galloway, et al., Interstitial Cystitis: A Form of Reflex Sympathetic Dystrophy?, In Press.

Robert G. Chuinard, M.D., et al., Intravenous Reserpine for Treatment of Reflex Sympathetic Dystrophy, Southern Medical Journal, vol. 74, No. 12, pp. 1481–1484, Dec. 1981.

Steven R. Ford, M.D., et al., The Treatment Oraflex Sympathetic Dystrophy with Intravenous Regional Bretylium, Anestesiology, vol. 68, No. 1, pp. 137–140, Jan. 1988.

William T. Hyland, M.D., Treating Reflex Sympathetic Dystrophy with Transdermal Nitroglycerin, Correspondence, vol. 83, No. 1, p. 195.

METHODS OF TREATING INTERSTITIAL CYSTITIS AND URETHRAL SYNDROME

BACKGROUND OF THE INVENTION

The present invention is directed to methods of treating mammalian interstitial cystitis and/or urethral syndrome, two painful lower urinary tract disorders for which there is no adequate treatment currently available. The methods generally comprise the administration of a pharmaceutically effective amount of Nifedipine ($C_{17}H_{18}N_2O_3$), a calcium channel antagonist which has been primarily used for the treatment of coronary artery disease and hypertension. Since Nifedipine provides effective relief with few side effects and is an oral medication that is well tolerated and relatively inexpensive, it is an attractive therapeutic agent for the treatment of these two painful voiding disorders.

More particularly, interstitial cystitial cystitis is a painful disease of the urinary bladder which is of unknown etiology and is most commonly seen in adult women. It is characterized by a number of urinary difficulties such as suprapubic pressure and pain with bladder filling, urinary frequency, nocturia, dysuria, urgency and irritative voiding asociated with morphological and histological changes in the bladder.

Urethral syndrome is a related painful voiding disorder of unknown etiology effecting women exhibiting many of the conditions set forth above. In this regard, while there are many similarities between the characteristics and conditions of these two voiding disorders, they exhibit a number of different characteristics. Specifically, interstitial cystitis is a condition consisting of a symptom complex with a specific voiding pattern (frequency, urgency, nocturia, lower abdomino-perineal pain and possibly dysuria), associated with glomerulations in response to bladder filling and, if present, a Hunner's ulcer. In contrast, patients with the urethral syndrome experience dysuria, urgency (usually with frequency) and sometimes abdominoperineal pain in the absence of nocturia and the cystoscopic findings consistent with interstitial cystitis.

As a result of the absence of a specific cause for, and unique histology of these disorders, no universally effective treatment processes or cures have been implemented. Along this line, there have been a multitude of proposed etiologies for interstitial cystitis, including the following: infection (Fall, M., Johansson, S. L. and Vahlne, A.: *J. Urol.*, 133:771-5, 1985; Gillespie, L. M. and Jones, J. F.: *J. Urol.*, 135:271A, 1986; and, Hunner, G. L.: Boston Med. *Surg. J.,*: 172:660-4, 1915), allergic or immune disorder (Oravisto, K. J.: *Eur. Urol.*, 6:10-3, 1980; Gordon, H. L. Rosen, R. D., Hersh, E. M., and Yium, J. J.: *J. Urol.*, 109:228-33, 1973; and, Matilla, J.: *Clin. Immun. Immunopath.*, 23:81-9, 1982), defective transitional mucosa (Parsons, C. L., Boychuk, D., Jones, S., Hurst, R. and Callahan, H.: *Invest. Urol.*, 143:139-42, 1990), endocrinologic disturbance (Powell, T. O.: *Surg. Gynecol. Obstet.*, 78:605-9, 1944), toxic urinary chemicals (Clemensen, O., Lose, G., Holm-Bentzen, M. and Colstrup, H.: *Urology*, 2:17-20, 1988), psychiatric disorder (Blaivas, S. and Blaivas, J. G.: *J. Urol.*, 135:189A, 1986), neurogenic disorder (Fall, M.: *J. Urol.*, 133:774-8, 1985), lymphatic obstruction (Coutts, W. E. and Vargas-Zalazar, R.: *Urol. Cut. Rev.*, 49:166-71, 1945) and vascular obstruction (Galloway, N. T. M., Gabale, B. R. and Irwin, P.: *Semin, Urol.*, 1991, (in press)), The current speculation regarding the cause of interstitial cystitis can be divided into two schools of thought: those who believe that the disease is caused primarily by a defect in the bladder mucosa, which may initiate an autoimmune response, and which may be exacerbated by the release of inflammatory mediators; and those who believe that the disease is a variant of reflex sympathetic dystrophy, an autonomic nerve-mediated ischemia known to affect limbs (Chuinard, R. G., Dabezies, E. J., Gould, J. S., Murphy, G. A. and Mathews, R. E.: *South Med. J.*, 74:1481-4, 1981), in which a subtle ischemia of the bladder is responsible for the mucosal defects and for the associated inflammation.

Regardless of the cause of interstitial cystitis, several investigators have shown that the inflammatory symptoms of this disease are associated with an immune response. Gordan and associates (Gordon, H. L., Rossen, R. D., Hersh, E. M. and Yium, J. J.: *J. Urol.*, 109:228-33, 1973) observed immunoglobulin deposits in the mucosal and submucosal layers of the bladder. Submucosal T-cell infiltrates were characterized by both Hanno and associates (Hanno, P., Levin, R. M., Monson, F. C., Teusher, C., Zhou, Z. Z., Ruggieri, M., Whitmore, K. and Wein, A. J.: *J. Urol.*, 143:278-81, 1990), and Christmas and Associates (Christmas, T. J., Rode, J., Bothazzo, G. F. and Milroy, E. J. G.: *Eur. Urol.*, 18:415-8, 1990). Witherow and associates (Witherow, R. O'N, Gillespie, L., McMullen, L., Goldin, R. D. and Walker, M. M.: *Br. J. Urol.*, 64:158-67, 1989) described an humoral immune response associated with submucosal B-cell infiltrates. The historical failure of immunosuppressant (or anti-inflammatory) therapy (Hanno, P. M. and Wein, A. J.: *Urology (suppl.)*, 29:22-26, 1987), however, suggests that interstitial cystitis is not primarily an autoimmune phenomenon.

Furthermore, some investigators have suggested that interstitial cystitis is a form of reflex sympathetic dystrophy (Galloway, N. T. M., Gabale, B. R. and Irwin, P.: "Interstitial Cystitis: A Form of Reflex Sympathetic Dystrophy?", *Semin. Urol.*, (in press)), a syndrome characterized by end-organ (limb) ischemia and pain which progresses to atrophy, all of which is secondary to a dysfunctional sympathetic nervous system reflex loop. In theory, reflex sympathetic dystrophy of the bladder may be initiated by any shock or insult to the bladder (direct trauma, infection or dysfunctional voiding) followed by a sympathetic nervous system constriction of the arteries to the detrusor muscle; the ischemic insult is perpetuated by dysfunctional voiding, perhaps in response to the pain caused by ischemia, and the ultimate consequence of this vicious spiral is a pale, contracted bladder (end-stage disease).

However, the relationship between the detrusor muscle and the pathogenesis of interstitial cystitis (i.e. the reflex sympathetic dystrophy theory) has been controversial. Perez-Marrero and associates (PerezMarrero, R., Emerson, L. E. and Juma, S.: *Urology (suppl.)*, 29:27-30, 1987) characterized 50 "interstitial cystitis" patients according to cystometric parameters: 13 of the 50 patients had uninhibited detrusor contractions, but no patient had a decrease in detrusor compliance. Contrary to these findings, the consensus report from the 1987 National Institutes of Health workshop (Gillenwater, J. Y. and Wein, A. J.: *J. Urol.*, 140:203-6, 1988) declared that involuntary detrusor contractions excludes the diagnosis of interstitial cystitis, and a decreased bladder compliance is 1 of the 4 "positive factors" which are used in establishing the diagnosis (2 of 4 positive factors require). Additionally, it is well-established that the symptoms of interstitial cystitis cannot be relieved to the patient's satisfaction by administering anticholinergic agents (Messing, E. M: In Walsh, P. C., Gittes, R. F., Perlmutter, A. D., Stamey, T. A. (eds): *Camobell's Urology.*, Philadelphia, W. B. Saunders Co., 1986, pp. 1070–86).

Calcium channel antagonists such as Verapamil, Diltiazem and Nifedipine inhibit intracellular shifts of calcium in a variety of cell types. As potent inhibitors of vascular smooth muscle contractions, calcium channel antagonists have been used primarily for the treatment of cardiovascular disorders such as hypertension and coronary artery disease (Stone, P. H., Antman, E. M., Mueller, J. E. and Braunwald, E.: *Ann Int. Med.*, 93:886–904, 1980). In small clinical trials Nifedipine yielded mixed results for the treatment of esophageal spasms (Richter, J. E., Dalton, C. B., Bradley, L. A. and Castell, D. O.: *Gastroent.*, 93:21–8, 1987) and for the relief of ureteral spasms (Viskin, S., Saver, I., Greenstein, A. and Hassner, A.: *Ann Int. Med.*, 105:142, 1986). Under experimental conditions calcium channel antagonists are known to inhibit detrusor muscle (bladder) contractions more effectively than anticholinergic agents (Zar, M. A., Irivani, M. M. and Luheshi, G. N.: *J. Urol.*, 143:835–9, 1990). Based on the results of these in vitro studies, a more efficient control of uninhibited detrusor contractions may have been possible by using a combination of anticholinergic and calcium channel blocking agents: both types of pharmacologic activities are present in Terodiline, but this drug had only limited clinical success in the treatment of patients with detrusor instability (Tapp, A., Fall, M., Norgaard, J., Massey, A., Choa, R., Carr, T., Korhonen, M. and Abrams, P.: *U. Urol.* 142:1027–31, 1989).

Calcium channel antagonists also affect the immune response by reducing the transport of calcium across lymphocyte cell membranes and by limiting the availability of calcium to immunoregulatory protein receptor sites. It has been shown that inhibition of the intracellular shift of calcium alone can suppress lymphocyte proliferation, even in the presence of lectins (Lindahl-Kisseling, K. M.: *Exp. Cell Research,* 103:151–7, 1976). Brix and associates (Brix, D. L., Berger, M. and Fleisher, T. A.: *J. Immunol.,* 133:2904–9, 1984) observed that both the interactions of IL-2 with its receptor and IL-2 mediated T-cell proliferation can be inhibited by Diltiazem, Verapamil or Nifedipine. Of particular relevance to this proposal are the data reported by Corteza and associates (Corteza, O., Shen, S., Revie, D. and Chretien, P.: *Transplant,* 47:339–42, 1989), who demonstrated variable effects on delayed-type hypersensitivity by the three classes of calcium channel antagonists in C3H mice: Diltiazem had no significant influence, Nifedipine suppressed delayed-type hypersensitivity, but Verapamil enhanced this type of immune response. In the event that an immune response may be responsible, in part, for some of the symptoms of interstitial cystitis, the observations of Corteza and associates lend some support to the choice by the present invention of Nifedipine over other calcium channel antagonists for the treatment of interstitial cystitis.

Nifedipine, therefore, has three potential mechanisms for influencing the voiding symptoms in patients with interstitial cystitis: detrusor muscle relaxation, vascular smooth muscle relaxation or immunosuppression. In view of the fact that the patients who fulfill the NIH criteria (Gillenwater, J. Y. and Wein, A. J. *J. Urol.,* 140:203–6, 1988) for this disease cannot have had a favorable response either to anti-spasmodic (bladder muscle relaxants) or to immunosuppressive agents alone (Messing, E. M.: in Walsh, P. C., Gittes, R. F., Perlmutter, A. D., Stamey, T. A. (eds): *Campbell's Urology.,* Philadelphia, W. B. Saunders Co., 1986, pp. 1070–86; and, Hanno, P. H. and Wein, A. J.: *J. Urol.,* 141:846–8, 1989), it was believed that Nifedipine would not have been a useful therapeutic agent for the treatment of interstitial cystitis and/or urethral syndrome.

However, as more clearly demonstrated below, Nifedipine has proven to be an effective therapeutic agent for the treatment of these two painful voiding disorders. While not wishing to be bound to any theory or mode of operation, it is the present inventor's opinion, which is not held widely by other urologists at this time, that interstitial cystitis is a variant of reflex sympathetic dystrophy, and that Nifedipine is effective, because it affects the vascular smooth muscle supply the bladder, and interrupts the abnormal reflex loop.

As a result, the present invention is directed to a new therapeutic process for treating mammalian interstitial cystitis and/or urethral syndrome. The objects and advantages of the present invention are more particularly set forth below.

SUMMARY OF THE INVENTION

According to the invention there is provided a method of treating mammalian interstitial cystitis and/or urethral syndrome through the use of Nifedipine, a calcium channel antagonist which has been primarily used for the treatment of coronary artery spasms and hypertension. Specifically, the invention is directed to the administration of a therapeutically effective amount of Nifedipine to mammals suffering from interstitial cystitis and/or urethral syndrome. The Nifedipine may be administered in admixture with a pharmaceutically acceptable carrier in a unit dosage form. The route of administration is that deemed preferred by the attending physician, with oral administration being preferred. The administered amount of Nifedipine varies depending upon the patient's response, the method of administration, body weight, age or individual characteristics of the subject being treated, the condition to be treated, its severity, and with its location. The preferred oral dose range for an adult human various between about 30 mg to about 60 mg daily. The Nifedipine can be released orally as an extended release tablet (single dose) or in divided doses of, for example, 10 mg or 20 mg soft gelatin capsules, 3 times a day.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art.

DETAILED DESCRIPTION OF THE INVENTION

Nifedipine, dimethyl 1,4-dihydro-2,6-dimethyl-4-(o-nitrophenyl)-3,5-pyridinedicarboxylate, $C_{17}H_{18}N_2O_6$, is a well known coronary vasodilator which has been used as a therapeutic agent for the treatment of coronary insufficiency, angina, hypertension and asthma.

Along this line, Nifedipine, as a calcium channel blocker compound, possesses outstanding vasodilating activity, especially cardiovasodilating effects, and hypotensive activity. As a result, Nifedipine is widely utilized as a vasodilating agent and a hypotensive medicament clinically for the remedy of angina pectoris and hypertension.

These disorders have in common a decrease in blood flow or availability, and as a common relief, an increase or easing of blood flow is induced by the vasodilatory effects produced by Nifedipine. Although calcium blockers or antagonists are generally unpredictable, Nifedipine has proven to be an effective therapeutic agent for those coronary and/or circulatory disorders.

Normally, Nifedipine is administered to patients via oral or parenteral routes. However, as a result of the relatively insolubility of Nifedipine in water and body fluids, its light sensitivity, as well as its rapid metabolization and excretion by the human body, pharmaceutical manufacturers have been actively involved in developing Nifedipine preparations with enhanced dissolution characteristics. See generally U.S. Pat. Nos. 3,485,847; 4,665,081; 4,749,714; 4,765,990; 4,855,300; 4,869,899; 4,871,545; 4,874,774; 4,892,730; 4,894,235; 4,880,523; and, 4,904,699.

In addition, apart from its use as a coronary vasodilator, Nifedipine has been found to be useful in the treatment of other diverse disorders such as viral infections (U.S. Pat. No. 4,800,081), tumors growth (U.S. Pat. No. 4,690,935), platelet hyperactivation, (U.S. Pat. No. 4,728,660) and central nervous system (CNS) disorders such as stroke (U.S. Pat. No. 4,696,934). However, to the present inventors knowledge, Nifedipine has not been utilized in the treatment of lower urinary tract disorders such as interstitial cystitis and/or urethral syndrome. The present invention relates to this discovery.

Specifically, the instant invention comprises of novel therapeutic methods for treating interstitial cystitis and/or urethral syndrome in a mammal which comprises administering a therapeutically effective amount of Nifedipine. The Nifedipine may be administered in admixture with pharmaceutically acceptable carriers adjuvants or excipients in a unit dosage form.

The route of administration, although not deemed to be critical, is generally orally, i.e. oesophageally. The oral route of administration of Nifedipine is preferred for convenience and self-medicating purposes. The administation of Nifedipine, whether orally, parenterally, etc., can be effective utilizing solid and liquid dosage unit forms either alone or in association with pharmaceutically acceptable carriers, binders, coloring agents, and other conventional additives. Generally, the solid form preparations includes powders, tablets, cachets, dispersible granules, capsules, granulates, and the like, while the liquid form preparations include solutions, suspensions and emulsions. In addition, if desired the Nifedipine preparation may be formulated in sustained release form. The overall formulations of such Nifedipine compositions are well known in the art, and the present invention is not directed to the specific Nifedipine compositions themselves, but to the specific method of utilizing these compositions to treat the painful bladder disorders indicated.

According to the preferred embodiment of invention, Nifedipine is administered in an effective amount which comprises a total oral dosage of Nifedipine of about 10 to about 80 mg, preferably about 30 to about 60 mg to a human adult patient suffering from interstitial cystitis and/or urethral syndrome. The daily dosages can be administered in a single amount, such as through an extended release table of 30 mg (Procardia ®, Nifedipine, Pfizer Laboratories, Pfizer, Inc., see The Merck Index, 10th Edition, registry No. 6374), or in divided doses of 10 mg or 20 mg soft gelatine capsules (Miles Labs., Inc. (subsidiary of Bayer A. G.), Elkhart, Ind.) administered three times a day. Variations within the three dosages may depend upon age, size, or individual characteristics of the patient being treated, as well as with the condition to be treated, its severity and with its location.

It has been determined that the method of the present invention is effective in treating mammals, particularly middle-aged women, exhibiting symptoms of interstitial cystitis and/or urethral syndrome. In this regard, the clinical and local immune response to Nifedipine was investigated in an open trail with 10 female interstitial cystitis patients, whose disease was diagnosed according to the consensus criteria developed in 1987 at a National Institutes of Health workshop. To objectify the symptoms and the clinical response of the patients the present inventors scored (scale 0 to 2) the symptoms of frequency, urgency, nocturia, dysuria and suprapubic pain (See Example 1 below). Nifedipine was administered as a single daily dose determined by a dose-titration test. Urinary interleukin-2 inhibitory activity (IL-2-IN), a marker of cell-mediated inflammation, was measured using a murine interleukin-2 dependent cell line.

Prior to Nifedipine therapy, the symptom scores (total of the 5 symptoms) ranged between 5 and 9; after 2 months, symptom scores ranged between 0 and 6. Of the 9 patients followed for at least 4 months, only 1 patient failed to have a significant clinical improvement, 5 patients showed at least a 50% reduction in symptom scores, and 3 patients were asymptomatic. Drug side-effects were minimal. Urinary IL-2-IN activity before Nifedipine therapy confirmed the presence of cell-mediated inflammation: after 4 months of therapy IL-2-IN activity was normal in 7 of 9 patients, regardless of the severity of symptoms, which indicated that Nifedipine exerted an immunosuppressive effect. The data suggested that Nifedipine is an efficacious, well-tolerated, convenient oral medication for the treatment of interstitial cystitis.

In addition, as more clearly demonstrated below in Example 2, the present inventors have also observed similar responses in regard to the treatment of urethral syndrome. As a result, the test data clearly indicates that Nifedipine is an effective therapeutic agent for the treatment of interstitial cystitis and/or urethral syndrome.

While once again not wanting to be limited to any theory or mode of operation, it is theorized that Nifedipine is effective primarily because it breaks an abnormal autonomic reflex loop affecting the bladder's vasculature, thereby reversing the subtle ischemia which is thought by the inventor to be the cause of interstitial cystitis and/or urethral syndrome. While it is also possible that the immosuppressive effect of Nifedipine helps relieve the symptoms exhibited by these two painful bladder disorders, the data set forth below in Example 1 suggests that immunosuppressive by Nifedipine can occur regardless of the lack of therapeutic benefit.

As a result, it has been found that Nifedipine is particularly well-suited for the treatment of interstitial cystitis and/or urethral syndrome because not only does it provide effective relief, it is available for oral administration and is relatively inexpensive. It has been discovered that patients receiving Nifedipine substantially reduce the pathological conditions exhibited by these two painful bladder disorders, and are able to carry on their daily activities in a relatively normal existence in comparison with their pre-treatment state.

The present invention will be further described according to the following non-limiting examples.

EXAMPLE 1

Materials and Methods

Patients The diagnosis of interstitial cystitis was assigned to 10 female patients, aged 23 to 51 years, in accordance with the consensus criteria established at the National Institutes of Health workshop on interstitial cystitis, August, 1987 (Gillenwater, J. Y. and Wein, A. J.: Summary of the National Institute of Arthritis, Diabetes, Digestive and Kidney Diseases Workshop on Interstitial Cystitis, National Institutes of Health, Bethesda, Md., Aug. 28-29, 1987, *J. Urol.*, 140:203, 1988):

| Interstitial Cystitis: Criteria for Diagnosis | |
|---|---|
| Inclusion Criteria | Exclusion Criteria |
| Hunner's Ulcer (if present, automatic inclusion) | less than 18 years old |
| | benign or malignant tumors |
| | radiation, tuberculous, bacterial |
| Positive Factors (at least 2 required for inclusion): | or cyclophosphamide cystitis |
| | vaginitis |
| | duration of symptoms <1 year |
| suprapubic, pelvic, urethral, vaginal or perineal pain | gynecologic cancer |
| | urethral diverticulum, bladder or lower ureteral calculi |
| glomerulations at cystoscopy after bladder distension | active herpes (HSV II) |
| | waking frequency <5 in 12 hrs. |
| (80 cm water pressure × 1 min.) | nocturia <2 |
| | neurogenic bladder dysfunction |
| decreased compliance on cystometrogram | waking capacity >400 ml, absence |
| | of urgency with bladder filling |
| | symptoms relieved by antibiotics, urinary |
| pain on bladder filling relieved by emptying | urinary analgesics or antiseptics |

Additional pertinent characteristics of the 10 patients involved in the investigation set forth in this example were as follows: no one had a Hunner's Ulcer; all failed an initial, empiric trial (4 weeks) of anticholinergic medication (oxybutinin); all received a trial of hydrodistension therapy, which provided no sustained relief of symptoms; and intravesical dimethylsulfoxide instillation therapy was used, without sustained success, in 2 patients. Bladder biopsies performed within 2 years prior to Nifedipine therapy showed chronic inflammation and varying degrees of submucosal mast cell infiltrations. One patient had a history of hypertension (treated with hydrochlorothiazide).

Cystometrics were performed after cessation of other modes of therapy and prior to institution of Nifedipine therapy: all patients had a waking bladder capacity of less than 350 ml (range 150 ml to 340 ml), 8 of 10 patients had a decreased bladder compliance and none had uninhibited contractions.

Symptom Evaluation: The symptom scores (total score range: 0 to 10) formed the basis for the evaluation of treatment efficacy. The severity of each symptom was assigned a numerical value, as follows:

| Symptom Severity Survey | | |
|---|---|---|
| Symptom | Description | Score |
| Frequency (daytime) | voids once every 3 to 5 hours | 0 |
| | voids once every 1 to 2 hours | 1 |
| | voids more than once every hour | 2 |
| Urgency | urge to void equal to actual frequency | 0 |
| | urge to void exceeds actual frequency | 1 |
| | constant urge to void | 2 |
| Nocturia | no nocturia, or 1 void nightly | 0 |
| | nocturia 2 to 4 times nightly | 1 |
| | more than 4 times nightly | 2 |
| Dysuria | no dysuria | 0 |
| | intermittent dysuria | 1 |
| | dysuria with each void | 2 |
| Suprapubic pain (abdomino-perineal) | no pain | 0 |
| | intermittent pain | 1 |
| | constant pain | 2 |

At the time of diagnosis, and before any treatment, any patient who falls within the parameters of the inclusion of exclusion descriptors of the NIH workshop consensus criteria (above) will score at least a "4" on this survey (frequency <1; urgency <1; nocturia <1; and either dysuria or suprapubic pain <1).

Urine Collection: Urine specimens were collected from all patients before and during Nifedipine therapy. Voided urine was centrifuged at 1000 ×g for 10 minutes at 4° C. and the supernatant separated from the sediment. The urine supernatant was subjected to 0.2 μ filtration at 4° C. (Nalgene, cellulose acetate) to remove any bacteria and debris, and a 1 ml aliquot was removed from creatinine measurement (Creatinine II Analyzer, Beckman, Brea, Calif.). The supernatant was ultrafiltered against 3 ×volume in phosphate-buffered saline (PBS) with 0.1 μg/ml albumin (Sigma, St. Louis, Mo.) using an Amicon filtration device (YM-5 membrane; 5,000 MW cut off; Amicon, Deavers, Mass.). The concentrated supernatant was dialyzed using 3,500 MW cutoff tubing (Spectrum, Los Angeles, Calif.), Shell frozen with dry ice and vacuum lyophilized. The powder was stored at −20° C.

Measurement of IL-2-IN Activity: The bioassay for IL-2-IN was modified from the method for measuring IL-2 activity described by Gillis and associates (Gillis, S., Fern, M. M. and Smith, K. A.: T-Cell Growth Factor: parameters of production and a quantitative microassay for activity. *J. Immunol.*, 120:2027, 1978). The murine IL-2-dependent cytotoxic T-cell line (CTLL-N) was derived from the CT-6 cell line, a gift of Dr. Claudio Fiocchi (Kusugami, J., Youngman, K. R., West, G. A. and Fiocchi, C: Intestinal immune reactivity to interleukin-2 differs among Crohn's disease, ulcerative colitis and controls, *Gastroent.*, 97:1, 1989). The CTLL-Ns were maintained in liquid culture using a 1:1 mixture of Roswell Park Memorial Institute (RPMI) 1640 and Dulbecco's Modified Eagles Medium (DMEM; 4.5 g/L glucose) media (Whittaker M. A. Bioproducts, Walkersville, Mass.) supplemented with 2.9 mg/ml glucose, 9.4 mM HEPES buffer, 1.9 mX l-glutamine, 289 μg/ml arginine, 0.12 M non-essential amino acids, 5 ×10(-E5) M 2-mercaptoethanol, 4.5% fetal bovine serum, 90 units/ml penicillin, 90 μg/ml streptomycin, 22 μg/ml fungizone, 0.45 mg/ml gentamicin and 20 units/ml of human recombinant IL-2 (CETUS Corp., Emeryville, Calif.).

The CTLL-Ns were washed and suspended at a concentration of 10(E5)/ml in the culture media. Assays were performed in triplicate, as follows: a serial dilution of the sample aliquot (50 µl), a 1:10 dilution of the human recombinant IL-2 standard and 10(E4) CTLL-Ns (100 µl) were placed in microliter wells. The microliter plates were incubated in a humidified 6% $CO_2$ atmosphere at 37° C. for 24 hrs., and the cells were pulsed at the 19th hour with 1 µCi/well of methyl-tritiated thymidine (spec. activity 6.7 Ci/mM, NEN, I. E. Dupont, Boston, Mass.).

The cells were collected onto glass filter paper discs using a PHD Cell Harvester (Cambridge Technology, Cambridge, Mass.). The discs were placed in Scintiverse (Fisher Scientific, Pittsburgh, Pa.) and thymidine uptake measured by liquid scintillation spectrophotometry. IL-2 inhibitory activity was calculated by modified probit analysis (software written by Robert S. Wallis).

The proliferation "maximum" was the tritiated thymidine uptake caused by the amount of exogenous IL-2 activity in the control microliter wells, assessed in quadruplicate for each assay. The proliferation "minimum" was derived from lowest amount of tritiated thymidine uptake caused by the IL-2 inhibitor standard. The probit calculation corrected for minor interassay variations of thymidine uptake in control wells, and permitted interassay comparisons of inhibitor activity among the urine samples. By this treatment of the data, the calculated value of IL-2 inhibitory activity in lyophilized urine samples varied less than 10% from assay to assay. IL-2-IN activity was expressed in units/mg urine creatinine (U/mg u.c.). IL-2-IN activity is less than 0.05 U/mg u.c. in the urine of healthy adults (Fleischmann, J. D., Acino, S. A., Riden, D. J., Thomas, K. T., Wentworth, D. B., Toossi, Z. and Ellner, J. J.: Measurement and Partial Characterization of an Interleukin-2 Inhibitor (IL-2-IN) in Human Urine, *J. Biol. Reoulators Homeostatic Agents*, 4:73, 1990).

Nifedioine Titration Test: Informed consent was obtained prior to administration of Nifedipine for the tolerance test and for subsequent therapy. The patent sat upright during the test. Following a baseline blood pressure measurement, the patient ingested a 10 mg capsule and blood pressure was monitored every 15 minutes. If there was no decrease in diastolic blood pressure greater than 10 mmHg after 1 hour, a second 10 mg capsule was ingested and blood pressure monitored for another hour (Richter, J. E., Dalton, C. B., Bradley, L. A. and Castell, D. O.: Oral Nifedipine in the treatment of noncardiac chest pain in patients with the nutcracker esophagus, *Gastroent.*, 93:21, 1987). All patients tolerated a single 10 mg test dose, and 4 patients tolerated 20 mg without a decline in diastolic blood pressure greater than 10 mmHg.

Medication Assignments: All patients were treated initially with a total daily dose of 30 mg, which was administered as a single, extended release tablet. Prompted by an insufficient relief of symptoms (or symptoms flare), the Nifedipine dose was escalated to 60 mg daily in 3 patients after 2 months and in a fourth patient after 5 months. This fourth patient initially had not tolerated a total of 20 mg during the test dose/blood pressure monitoring, but did tolerate a 10 mg test dose after four months of therapy (while continuing to receive 30 mg daily) without a significant drop in blood pressure.

Patient Monitoring: Patients were interviewed and blood pressure measured twice monthly during the first 2 months of therapy, during the first 2 months after a dose escalation, and then once monthly thereafter. The symptom severity score at each interview was based on the patient's experiences during the previous 24 hours. All were under the care of 1 physician and all premenopausal patients exercised non-medicinal birth control during Nifedipine therapy.

Results

Clinical Response to Nifedipine: As shown in Table 1 below, baseline symptom scores (total of the 5 symptoms) for the 10 patients ranged between 5 and 9; after 2 months, symptom scores ranged between 0 and 9, and after 4 months, symptom scores ranged between 0 and 5. Of the 9 patients followed for at least 4 months, only 1 failed to show at least a 50% improvement. No patient whose total symptom score was less than 4 had severe symptoms (score: "2") in any of the 5 categories. The inventors observed that the first favorable effects of Nifedipine were the relief of pain, followed by a decline in urgency. Voiding frequency and nocturia were the symptoms most resistant to therapy. Patient 4 was asymptomatic for 3 months consecutively, the 30 mg daily dose of Nifedipine was reduced to an every other day dose, and the patient has remained symptom-free to date (2 months follow-up).

TABLE 1

| | Response to Nifedipine: Symptom Scores and Urinary IL-2-IN Activity | | | | | |
|---|---|---|---|---|---|---|
| | Pre-Therapy | | Month 2 | | Month 4 | |
| Patient | Symptom Score | UL-2-IN U/mg u.c. | Symptom Score | IL-2-IN U/Mg u.c. | Symptom Score | IL-2-IN U/mg u.c. |
| 1 | 5 | 0.11 | 1 | 0 | 0 | 0 |
| 2 | 7 | 0.21 | 4 | 0.17 | 2 | 0 |
| 3 | 6 | 0.32 | 2 | 0 | LOST TO FOLLOW-UP | |
| 4 | 5 | 0.15 | 0 | 0 | 0 | 0 |
| 5 | 6 | 0.80 | 8 | 1.6 | 5 | 0 |
| 6 | 8 | 0.22 | 3 | 0.04 | 2 | 0.08 |
| 7 | 7 | 0.10 | 9 | 0 | 3 | 0.08 |
| 8 | 8 | 0 | 5 | 0 | 4 | 0 |
| 9 | 9 | 0.05 | 6 | 0 | 2 | 0 |
| 10 | 5 | 0.19 | 7 | 0 | 0 | 0 |
| mean= | 6.6 | 0.22 | 4.5 | 0.18 | 2.0 | 0.02 |
| S.E.± | 0.45 | 0.07 | 0.96 | 0.16 | 0.60 | 0.01 |

Insufficient relief of symptoms (or symptom "flares") occurred in 3 patients at 2 months and in 1 patient at 5 months (see Table 2 below). According to the initial Nifedipine titration test, the first 3 of these 4 patients were eligible for 60 mg daily. Following the dose escalation, these 3 patients (nos. 5, 7 and 10) showed marked improvement, but 1 patient (no. 5) requested a return to 30 mg daily due to dizziness, and her symptoms worsened. Although not eligible initially for 60 mg daily, the fourth patient (no. 8) ingested a 10 mg test capsule (while maintaining the 30 mg daily dose) and the diastolic blood pressure did not fall more than 10 mmHg; her dose was increased in 60 mg daily, and her symptoms improved without untoward side-effects.

TABLE 2

Response to Nifedipine Following Dose Escalation
Symptom Scores

| Pt. | Month: 0 | 1 | 2 | 3 | 4 | 5 | 6 | 7 |
|---|---|---|---|---|---|---|---|---|
| 5 | 6 | 3 | 8* | 2+ | 5 | 6 | 5 | 5 |
| 7 | 7 | 2 | 9* | 4 | 3 | 3 | | |
| 8 | 8 | 3 | 5 | 4 | 4 | 6* | 3 | 3 |
| 10 | 5 | 1 | 7* | 2 | 0 | 1 | 0 | |

(* = dose escalation, + = dose reduction)

Drug-Related Effects: Drug side-effects occurred in 5 patients during the first month of therapy: headaches in 2 patients, dizziness in 2 patients and constipation in 1 patient. Headaches were relieved by over-the-counter analgesics, dizziness was transient and relieved by postural changes, and constipation was relieved by administration of a stool softener (for 2 weeks) and by dietary modification. No patient stopped taking Nifedipine due to the side-effects. As mentioned above, however, 1 patient (no. 5) whose dose was escalated to 60 mg daily requested a return to a 30 mg daily dose because of dizziness.

Urinary Interleukin-2 Inhibitor Levels: As shown above in Table 1, baseline interleukin-2 inhibitor (IL-2-IN) levels varied between 0 and 0.8 U/mg u.c. The levels of urinary IL-2-IN activity did not correlate with the baseline symptom scores, and a given IL-2-IN level could not be used to predict the severity of symptoms at any time. A transient rise in urinary IL-2-IN activity relative to the baseline correlated with a worsening of symptoms in 2 patients (1 not shown), and did not rise from 0 during the period of monitoring in 1 patient. Given these exceptions, baseline urinary IL-2-IN levels declined significantly in 9 of 10 patients during Nifedipine therapy. Urinary IL-2-IN levels were 0 in 7 patients after 4 months: in the 3 patients who were asymptomatic (symptom score =0) and in 4 patients whose symptom scores ranged between 2 and 5.

The effects of Nifedipine on smooth muscle and on the immune system in patients with interstitial cystitis appear to be complimentary, and may have provided further insight into the etiology of this disease. Regardless of its mechanism of action, the data set forth above suggests that Nifedipine has considerable promise as an agent for the treatment of interstitial cystitis.

EXAMPLE 2

In addition to the treatment of patients with interstitial cystitis, 6 patients with the urethral syndrome have been treated with Nifedipine, using the titration test and treatment protocol described above. At the time of this submission, four patients showed improvement and 2 patients showed little or no improvement. Of the patients who showed improvement (after 1 to 3 months of medication), 2 are being weaned from medication (1 is completely symptom-free), and 2 symptom-free patients have been off medication for 3 to 5 months, respectively. Similar to the data presented above, the positive response to Nifedipine in this limited study supports the hypothesis that the urethral syndrome and interstitial cystitis are both part of the same disease spectrum, perhaps as variants of reflex sympathetic dystrophy.

Thus, in view of the observations set forth above, the examples clearly indicate a heretofore unknown discovery that Nifedipine is an effective therapeutic agent for the treatment of interstitial cystitis and/or urethral syndrome.

The invention has been described with reference to the preferred embodiment. Obviously, modifications and alterations will occur to others upon a reading and understanding of this specification. It is intended to include all such modifications and alterations insofar as they come within the scope of the appended claims or the equivalents thereof.

Having thus described our invention, we claim:

1. A method for treating interstitial cystitis comprising the steps of administering to a living subject exhibiting the pathological conditions asociated with interstitial cystitis produced by autonomic nerve-mediated ischemia of the bladder a sufficient amount of Nifedipine to interrupt the abnormal autonomic reflex loop affecting the subject's bladder vasculature, thereby reversing the ischemia, wherein the administered amount of Nifedipine is from about 10 to about 80 mg which is administered daily for a period of time greater than four weeks.

2. A method for treating urethral syndrome comprising the steps of administering to a living subject exhibiting the pathological conditions asociated with urethral syndrome produced by autonomic nerve-mediated ischemia of the urethra a sufficient amount of Nifedipine to interrupt the abnormal autonomic reflex loop affecting the subject's urethra vasculature, thereby reversing the ischemia, wherein the administered amount of Nifedipine is from about 10 to about 80 mg which is administered daily for a period of time greater than four weeks.

* * * * *